United States Patent [19]

Maasz et al.

[11] Patent Number: 5,776,505
[45] Date of Patent: Jul. 7, 1998

[54] PHARMACEUTICAL COMBINATION PREPARATION COMPRISING KETOPROFEN

[75] Inventors: Joachim Maasz, Convent Station, N.J.; Ingrid Hürner, Leverkusen, Germany; Peter Kurka, Langenfeld, Germany; Ralph Lange, Wülfrath, Germany

[73] Assignee: Bayer Aktiengesellschaft, Leverkusen, Germany

[21] Appl. No.: 708,024

[22] Filed: Aug. 30, 1996

[30] Foreign Application Priority Data

Sep. 8, 1995 [DE] Germany ............... 195 33 162.1

[51] Int. Cl.⁶ .................... A61K 33/10; A61K 33/08; A61K 31/19
[52] U.S. Cl. .................... 424/686; 424/688; 424/692; 514/570
[58] Field of Search ................ 514/570; 424/686, 424/688, 692

[56] References Cited

U.S. PATENT DOCUMENTS

| | | | |
|---|---|---|---|
| 4,344,929 | 8/1982 | Bonsen et al. | 424/15 |
| 4,942,039 | 7/1990 | Duvall et al. | 424/466 |

FOREIGN PATENT DOCUMENTS

| | | |
|---|---|---|
| 0 465 235 | 1/1992 | European Pat. Off. . |
| 0 465 235 A1 | 1/1992 | European Pat. Off. . |
| 0 526 862 A1 | 2/1993 | European Pat. Off. . |
| 8907439 | 8/1989 | WIPO . |

OTHER PUBLICATIONS

P.J. Neuvonen, Br. J. Clin. Pharmoc., vol. 31, pp. 263–266 (1991).

P.F. D'Arcy, et al., Drug Intelligence and Clincal Pharmacy, vol. 21, pp. 607–617 (1987).

Neuvonen et al. Clin. Pharmacokinet. 27, No. 2 pp. 120–128, 1994.

Neuvonen, Br. J. Clin. Pharmacol 31(3) pp. 263–266, 1991.

*Primary Examiner*—Raymond Henley, III
*Attorney, Agent, or Firm*—Sprung Kramer Schaefer & Briscoe

[57] ABSTRACT

The invention relates to the combined use of ketoprofen and specific inorganic basic substances with an improved quality of action.

8 Claims, 3 Drawing Sheets

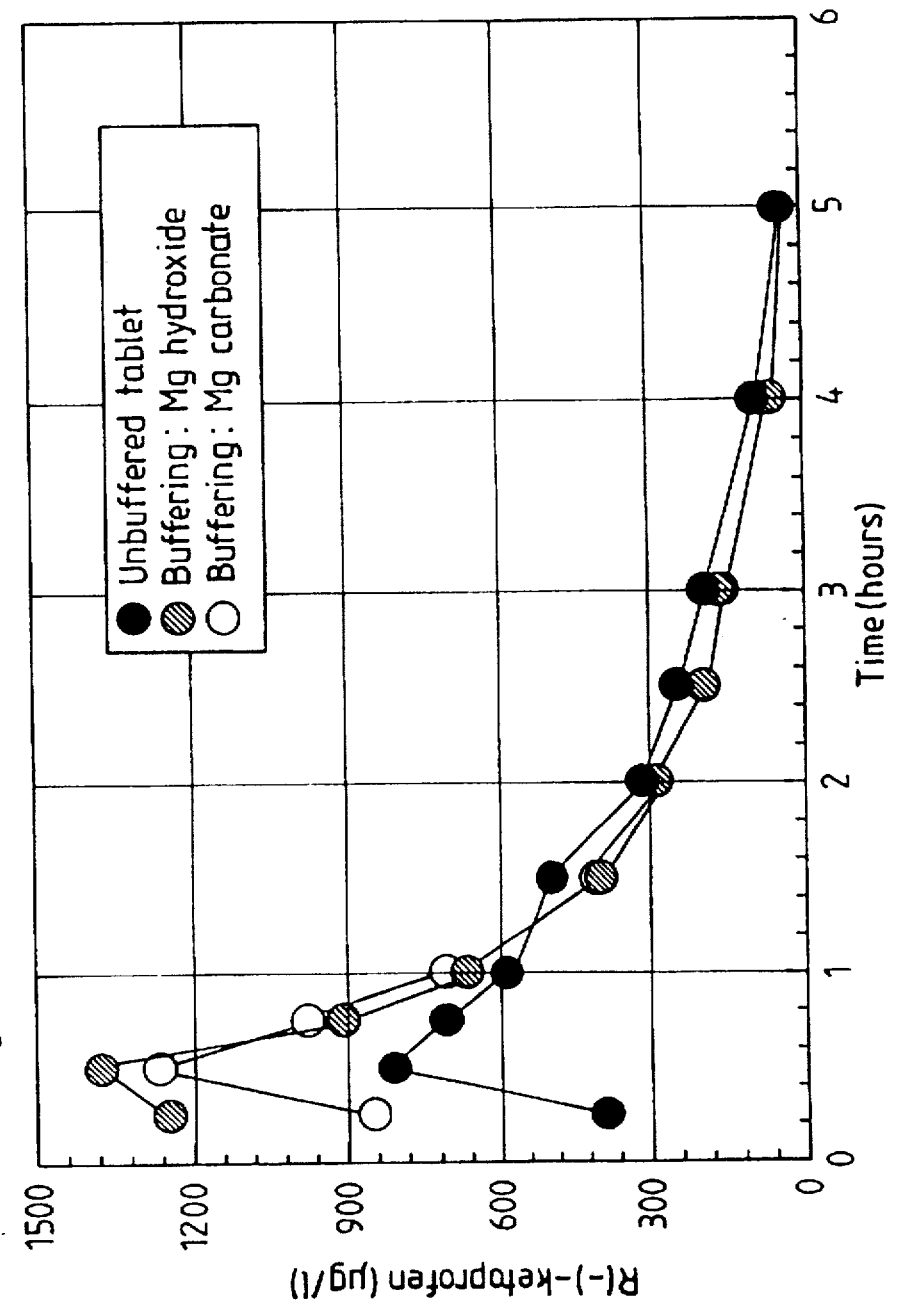

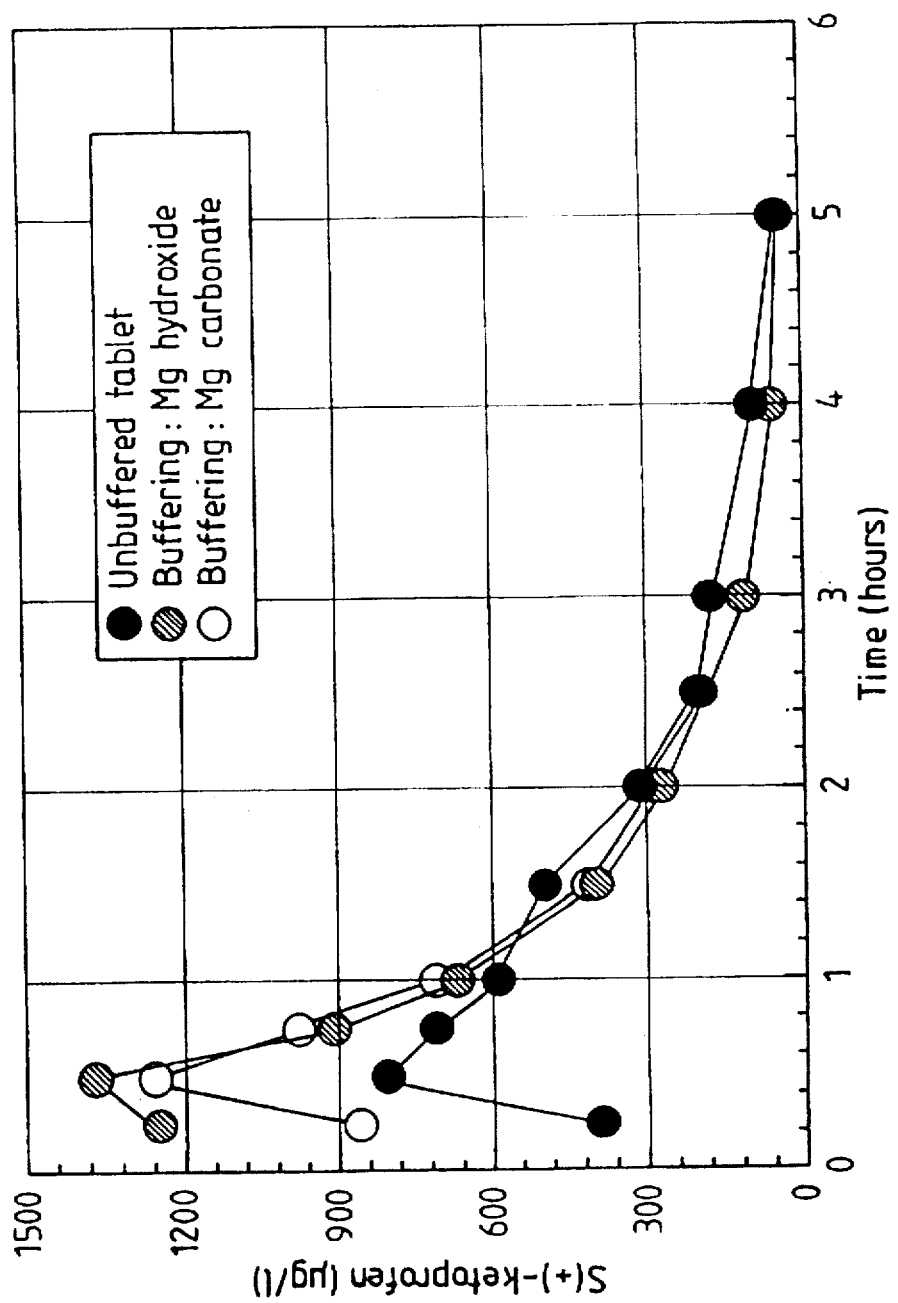

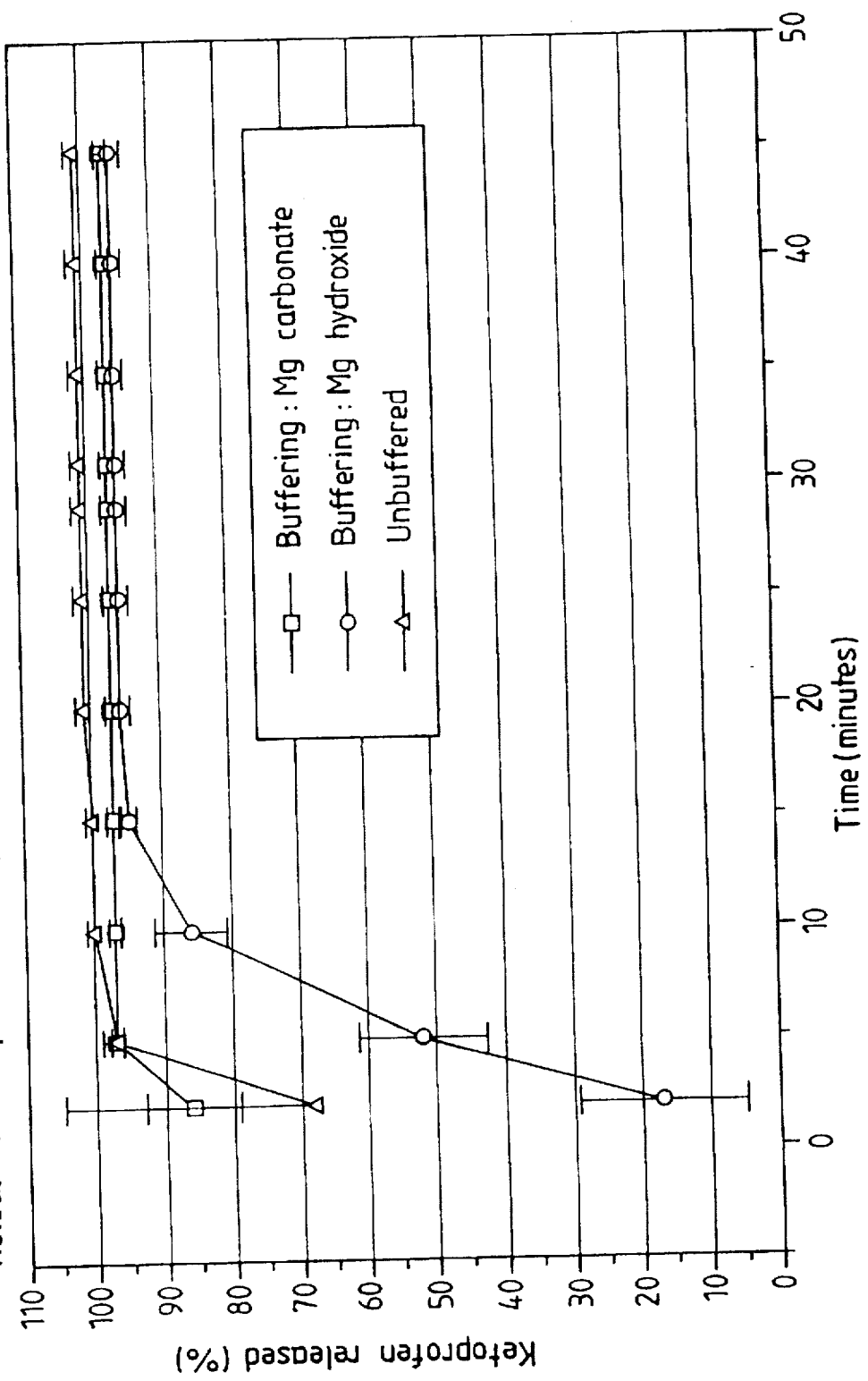

PHARMACEUTICAL COMBINATION PREPARATION COMPRISING KETOPROFEN

BACKGROUND OF THE INVENTION

The invention relates to the combined use of ketoprofen and special inorganic basic substances with an improved quality of action.

It is already known that basic substances such as magnesium hydroxide, magnesium oxide and sodium bicarbonate or mixtures thereof have an influence on the absorption of certain active compounds, such as anthranilic acid derivatives, propionic acid derivatives, acetic acid derivatives, salicylic acid derivatives or salts thereof or pyrazolols or benzothiazine derivatives (cf. Neuvonen WO 89/07439). In this Application, ketoprofen is also mentioned as an example of a propionic acid derivative.

It is also known to the expert that the absorption-regulating effect of certain additives cannot be generalized for all active compounds (cf. D'Arcy et al., Drug Intelligence and Clinical Pharmacy, 21, 607 (1987)). The granted claims of the abovementioned PCT Application by Neuvonen were limited to the specific active compounds tolfenamic acid, mefenamic acid -and ibuprofen, and only magnesium hydroxide and magnesium oxide are claimed as basic partners in the combination. This confirms the statement in the publication by D'Arcy et al. that the action of basic substances such as antacids on the absorption properties of active compounds cannot be predicted. The later publication by Neuvonen in Br. J. Clin. Pharmac. 31, 263 (1991) also shows, with the aid of two cross-over studies, that a higher plasma concentration occurs as a result of addition of magnesium hydroxide only in the case of ibuprofen. In the case of ketoprofen, neither a significant increase in the rate of absorption nor an increased extent of absorption was found.

SUMMARY OF INVENTION

Knowing of this prior art, it was not to be expected that by combining ketoprofen in racemic form and in the form of its S(+) and R(−) enantiomers with basic auxiliaries such as magnesium hydroxide and magnesium carbonate, a faster action and a significant increase in the maximum plasma level is achieved as compared with unbuffered tablets.

DETAILED DESCRIPTION OF THE DRAWINGS

FIGS. 1 and 2 show the plasma concentration of R(−)- and S(+)- ketoprofens respectively following administration of buffered verses unbuffered ketoprofen tablets.

FIG. 3 shows the rate of ketoprofen release over time of buffered verses unbuffered ketoprofen tablets.

DETAILED DESCRIPTION OF THE INVENTION

As shown in FIG. 1 and FIG. 2, a significant increase in maximum plasma level and a faster action is achieved using the buffered ketoprofen tablets of the invention versus the unbuffered tablets.

The absorption-accelerating action of magnesium hydroxide and magnesium carbonate can be seen from the $C_{max}$ AUC ratio according to Table 1.

Furthermore, the region of the $t_{max}$ values starts earlier in the case of the buffered tablets of the combination according to the invention, and shows less scatter than in the case of the unbuffered tablets. The comparative studies also show that the interindividual variation in the individual plasma levels is smaller in the case of the buffered combination tablets according to the invention than in the case of the unbuffered tablets.

The differences found in the maximum plasma concentrations ($C_{max}$) of the three different tablet formulations are significant. The ketoprofen tablet buffered with magnesium hydroxide in particular leads to higher plasma concentrations of the ketoprofen being achieved earlier than with the unbuffered tablet. In pain indication in particular, it is therefore advisable to use the buffered tablets with their faster onset of action compared with the unbuffered tablets.

The inventive step not only lies in overcoming the prejudice known from the literature that the absorption of ketoprofen cannot be influenced positively by basic substances, but is also intensified by our own in vitro test. A study of the release from ketoprofen tablets (25 mg) in vitro shows that the formulation with the combination of ketoprofen and magnesium hydroxide has the slowest release, as can be seen from FIG. 3. From these negative in vitro results, it was not to be expected that the combination of ketoprofen + magnesium hydroxide in particular shows such advantageous absorption properties in vivo.

Fixed combinations according to the invention which are of particular interest are those in the form of tablets, effervescent tablets, capsules, granules, powder mixtures, suspensions, emulsions and drops, which preferably comprise 1 part by weight of ketoprofen racemate or S(+)- ketoprofen or R(-)- ketoprofen in pure form or as mixtures in a weight ratio of 1 to 99 to 99 to 1, and comprise 1 to 25 parts by weight of the basic buffering additive, in particular magnesium hydroxide.

The buffer capacity of the basic partner of the combination in the presentation forms according to the invention is preferably at least 3 milliequivalents (meq).

Oral administration forms having a low individual scatter of the plasma concentrations, an increased rate of absorption and a higher maximum plasma concentration are preferred.

The fixed combinations according to the invention are prepared by customary methods, for example by mixing and subsequent pressing or by dissolving the individual components.

EMBODIMENT EXAMPLES

Example 1

The substances of Example 1 are processed to a tablet which releases ketoprofen at a moderate rate in vitro.

| Non-lacquered tablet | |
|---|---|
| Ketoprofen (racemate) | 25.0 mg |
| Magnesium hydroxide | 150.4 mg |
| Colloidal silicic acid | 12.0 mg |
| Sodium carboxymethyl-starch | 7.0 mg |
| Sodium citrate, tertiary | 50.0 mg |
| Magnesium stearate | 0.6 mg |
| Coating shell | |
| HPM cellulose | 1.2 mg |
| Polyethylene glycol 4000 | 0.4 mg |
| Titanium dioxide | 0.4 mg |
| Total weight | 147.0 mg |

Peparation

The ketoprofen, magnesium hydroxide, sodium carboxymethyl-starch and sodium citrate are granulated under aqueous conditions and then dried.

The remainder of the constituents (colloidal silicic acid, magnesium stearate) are admixed to these granules and this mixture is pressed to tablets of 8 mm diameter on suitable tablet presses.

Example 1a and 1b

Tablets comprising S(+)- and R(-)- ketoprofen are prepared in an analogous manner.

Example 2

The substances of Example 2 are processed to a tablet which releases ketoprofen rapidly in vitro.

| Non-coated tablet | |
|---|---|
| Ketoprofen (racemate) | 25.0 mg |
| Magnesium carbonate, basic | 258.0 mg |
| Sodium carboxymethyl-starch | 10.0 mg |
| Polyvinylpyrrolidone 25 | 7.4 mg |
| Colloidal silicic acid | 2.0 mg |
| Magnesium stearate | 0.6 mg |
| Coating shell | |
| HPM cellulose | 1.8 mg |
| Polyethylene glycol 4000 | 0.6 mg |
| Titanium dioxide | 0.6 mg |
| Total weight | 306.0 mg |

Preparation

The ketoprofen, magnesium carbonate, sodium carboxymethyl-starch and PVP are granulated under aqueous conditions and then dried.

The remainder of the constituents (colloidal silicic acid, magnesium stearate) are added to these granules and this mixture is pressed to tablets of 9 mm diameter on suitable tablet presses.

Comparison Example 3 (without buffer)

The substances of Example 3 are processed to a tablet which releases ketoprofen rapidly in vitro. The tablet comprises no buffering additive.

| | |
|---|---|
| Ketoprofen (racemate) | 25.0 mg |
| Maize starch | 48.0 mg |
| Avicel | 30.0 mg |
| Lactose | 32.0 mg |
| Sodium carboxymethylcellulose (Ac-Di-Sol) | 4.3 mg |
| Magnesium stearate | 0.7 mg |
| Coating shell | |
| HPM cellulose | 0.6 mg |
| Polyethylene glycol 4000 | 0.2 mg |
| Titanium dioxide | 0.2 mg |
| Total weight | 141.0 mg |

Preparation

The ketoprofen, maize starch, Avicel, lactose and Ac-Di-Sol are granulated under aqueous conditions and then dried.

These granules are mixed with magnesium stearate and pressed to tablets of 7 mm diameter on suitable tablet presses.

TABLE 1

| Parameter | Unbuffered tablet | | Buffered tablet ($Mg(OH)_2$) | | Buffered tablet ($MgCO_3$) | |
|---|---|---|---|---|---|---|
| | R(-)-ketoprofen | S(+)-ketoprofen | R(-)-ketoprofen | S(+)-ketoprofen | R(-)-ketoprofen | S(+)-ketoprofen |
| $C_{max}$/AUC (1 h) | 0.60 | 0.61 | 0.84 | 0.87 | 0.74 | 0.75 |

We claim:

1. A process for accelerating the absorption of ketoprofen in vivo which comprises combining 1 part by weight of ketoprofen with 1 to 25 parts by weight of an inorganic buffer substance of magnesium hydroxide, magnesium oxide or magnesium carbonate into a buffered administration form and orally administrating the so combined ketoprofen and buffer.

2. A process according to claim 1, wherein the active compound is ketoprofen in the form of its enantiomers S(+)- or R(-)- ketoprofen in pure form or as mixtures in a ratio of 1:99 to 99:1.

3. A process according to claim 1, wherein the buffer substance is at least one of magnesium oxide and magnesium hydroxide.

4. A process according to claim 1, wherein the buffer substance is magnesium oxide.

5. A Process according to claim 1, wherein said combination is in the form of tablets, capsules, granules, powder mixtures or suspensions.

6. A process for accelerating the absorption of ketoprofen in vivo which comprises combining ketoprofen with magnesium hydroxide in a buffered administration form and orally administrating the so combined ketoprofen and magnesium hydroxide.

7. A process according to claim 6, wherein the active compound is ketoprofen in the form of its enantiomers S(+)- or R(-)- ketoprofen in pure form or as mixtures in a ratio of 1:99 to 99:1.

8. A process according to claim 6, wherein said combination is in the form of tablets, capsules, granules, powder mixtures or suspensions.

* * * * *